United States Patent [19]

Dougherty

[11] 3,947,563

[45] Mar. 30, 1976

[54] HYDROGENOLYSIS OF FORMATES

[75] Inventor: Edward F. Dougherty, Corpus Christi, Tex.

[73] Assignee: Celanese Corporation, New York, N.Y.

[22] Filed: Oct. 7, 1974

[21] Appl. No.: 512,598

[52] U.S. Cl. ............ 423/636; 260/638 A; 423/641
[51] Int. Cl.² C01B 13/14; C01D 1/00; C07C 29/00
[58] Field of Search.................. 423/635, 636, 641; 260/638 A

[56] References Cited
UNITED STATES PATENTS

| | | | |
|---|---|---|---|
| 3,280,199 | 10/1966 | Schmerling | 260/638 A |
| 3,412,042 | 11/1968 | Kudo et al. | 260/638 A |
| 3,478,112 | 11/1969 | Adam et al. | 260/638 A |
| 3,736,265 | 5/1973 | Soggitt | 260/638 A |
| 3,752,861 | 8/1973 | Hobbs et al. | 260/638 A |

*Primary Examiner*—Oscar R. Vertiz
*Assistant Examiner*—Wayne A. Langel
*Attorney, Agent, or Firm*—Stewart N. Rice; Ralph M. Pritchett

[57] ABSTRACT

Process for hydrogenolysis of an alkali metal or an alkaline earth metal salt of formic acid so as to produce methanol and a metal hydroxide corresponding to the formic acid salt wherein a catalyst of cobalt, rhenium, ruthenium, palladium, platinum or mixtures thereof is used.

11 Claims, No Drawings

HYDROGENOLYSIS OF FORMATES

BACKGROUND OF THE INVENTION

In various industrial processes such as that for the production of pentaerythritol by reacting formaldehyde with acetaldehyde in the presence of an alkaline condensing agent, typically an alkali or alkaline earth metal hydroxide, there results a by-product stream of an alkali or alkaline earth metal salt of formic acid. These formates result from a reaction between the alkaline condensing agent and the formic acid formed in the reaction. At the present time no general use is known for sodium formate and therefore it is not readily marketable. These by-product formate streams are thus usually discarded. In order to avoid losses of material it is of course desirable that such formates be converted to more usable products, it being particularly desirable to recover the metal values and the carbon values in the formate.

It is thus an object of the present invention to provide a process for the treatment of an alkali metal or alkaline earth metal salt of formic acid so as to convert such to one or more products which are more desirable than the formate itself. It is a particular object of the present invention to provide a method for treating an alkali metal or alkaline earth metal formate so as to convert it to products including methanol and an alkali or alkaline earth metal hydroxide. Additional objects will become apparent from the following description of the present invention.

SUMMARY

The foregoing and additional objects are accomplished by the present invention which in one of its aspects is a process for hydrogenolysis of an alkali metal or alkaline earth metal salt of formic acid, which process comprises: in a reaction zone contacting a liquid phase solution of said salt of formic acid with hydrogen in contact with a catalyst having a catalytically active surface comprised of metallic cobalt, rhenium, ruthenium, palladium, or platinum or mixtures thereof, said reaction zone being maintained at elevated temperatures and pressures sufficient to cause reaction of said salt of formic acid with said hydrogen to form methanol and a hydroxide of said alkali metal or alkaline earth metal.

DETAILED DESCRIPTION OF THE INVENTION

The present invention may be utilized to convert alkali metal salts or alkaline earth metal salts of formic acid. The metal portion of the salt will thus, when an alkali metal, be sodium, potassium or lithium, and, when an alkaline earth metal, be calcium, barium, strontium or magnesium. The present invention is however especially suitable in the hydrogenolysis of sodium formate.

In order to accomplish the hydrogenolysis of the present invention, the formate must be in liquid solution, and, the solvent medium utilized may be any which is substantially inert under the reaction conditions in the reaction zone. By "substantially inert" is meant that the solvent does not react with itself of with the other components present in the reaction zone (including reactants and products) to a substantial extent, and, does not otherwise interfere or hinder the desired hydrogenolysis reaction. The solvent does not have to be totally inert since even the preferred solvent, water, will react somewhat with various of the components present in the reaction zone. Generally recommended as a solvent medium is water, an ether, an alcohol, or mixtures thereof. Ethers that may be used include the cyclic and acyclic ethers. Preferred are the alkyl ethers, both cyclic and acyclic, and the alkyl alcohols. Specific suitable solvents in addition to water are diethyl ether, ethyl butyl ether, methanol, ethanol, hexanol, 1,3 or 1,4 dioxane, tetrahydrofuran, and petroleum ether. The metal formate, which is normally a solid, may be dissolved in a solvent prior to the hydrogenolysis or a solution of the formate which is the by-product of another process may be utilized. The process is especially suited for treatment of those aqueous formate solutions derived from the above described processes for production of pentaerythritol by aldol condensation. The concentration of the formate in solution may vary widely and may be up to solubility limits and as low as one percent by weight or even lower with the preferred concentration being 5 to 25% by weight. It is pointed out that the aqueous metal formate being treated may, and frequently will, contain various other compounds as impurities such as pentaerythritol and sodium sulfate. Such impurities do not interfere with the hydrogenolysis of the present invention.

To carry out the process, the solution of the formate is in general contacted with hydrogen while also in contact with the catalyst. The formate solution and hydrogen may be led over a fixed bed of the catalyst or the catalyst may be slurried with the formate solution and the resulting slurry contacted with the hydrogen. The hydrogen itself may be led cocurrently or countercurrently. As a general rule technically pure hydrogen will be utilized but it is also possible to use gases rich in hydrogen, such as coke oven gas, water gas or town gas. The reaction of the hydrogen with the metal formate in accordance with the present invention will produce as major products methanol and a metal hydroxide corresponding to the metal of the formate, although various by-products will usually also be produced in side reactions. These by-products include carbon dioxide as well as metal carbonate corresponding to the metal of the formate. It is thought that a side reaction involves the reaction of hydrogen and the metal formate to form carbon dioxide and a metal hydroxide some of which in turn react and form the metal carbonate. Also it appears that some of the methanol formed in the main reaction will be reduced by reaction with hydrogen so as to form methane and water.

The hydrogenolysis reaction needs to be carried out at elevated temperatures and pressures sufficient to cause the desired production of methanol and the metal hydroxide. Generally temperatures within the range of 100°C to 300°C may be used, the preferable range being from about 175°C to 275°C. At temperatures in excess of 300°C it has been found that the above mentioned reduction of the methanol by hydrogen will unduly occur. Superatmospheric pressures are necessary, those within the range of 75 to 500 atmospheres absolute being generally utilized, with preferred ranges being 125 to 400 atmospheres absolute. The contact time or residence time in a batch process may vary widely with good conversions being realized under some conditions after about an hour or less, with usual residence times being about one to five hours; however longer residence times up to seven or more hours give significant yields. In a fixed bed process, the flow rate of liquid feed may vary widely, e.g. from 100 to 2000 milliliters per hour per liter of catalyst. Obviously the concentration, temperature, pressure, and catalyst composition will greatly affect such. Thus the foregoing range is not to be taken as limiting the scope of the present invention.

The catalysts used in the process are those metallic catalysts of cobalt, rhenium, ruthenium, palladium or platinum. Also mixtures of these may be used. Cobalt is the preferred catalyst. The method of making the catalyst does not comprise a part of the present invention as the catalysts are well known and are generally commercially available. The main requirement is that the catalyst have a surface containing the metallic cobalt or the like being used. The metallic catalyst may be prepared such as by in situ reduction of a metal salt in the hydrogenolysis reactor under reaction conditions or by an ex situ reduction prior to the hydrogenolysis. Metal salts or compounds that may be reduced include oxides, sulfides, selenides, various complexes and the like, including those that have been formed by sintering, that is by heating to temperatures above 600°C, preferably above 800°C, and preferably in the presence of oxygen. The production of a sintered catalyst is disclosed in U.S. Pat. No. 3,344,196 issued on Sept. 26, 1967 to Corr, et al. The catalysts known as "blacks" are also suitable, such as rhenium black and cobalt black. The reason for stating that the catalyst has a catalytically active surface comprised of the metallic cobalt, rhenium, or the like is that it is not known whether reduction of a metal oxide serves to reduce all of the oxide or merely that on the surface. In a solid catalyst it is generally the surface of a catalyst particle which is effective as a catalyst and not the interior of the particle.

The metallic catalyst may be supported on carrier substances such as pumice, alumina, kieselguhr, silica gel, synthetic silicates, porcelain, quartz and the like. The size and shape of the catalyst particles are not critical. For example, the catalyst may be in the form of pellets, powder, pills, saddles, spheres, etc. Also, reactor size has no bearing on the operation of the invention but it is presumed that the optimum size to give the proper residence time (as is usual in a hydrogenolysis reaction) is used. Reactors of conventional configuration may be used.

Following the hydrogenolysis reaction, the reaction products may be separated into the desired components by conventional means. For example the product stream from the reactor, after venting any hydrogen, could be fed to a distillation tower with the methanol being removed as light ends and the metal hydroxide removed as the residue stream.

EXAMPLE

A 150 milliliter rocking autoclave was charged with 10 milliliters of an aqueous sodium formate solution derived from the production of pentaerythritol, and containing 25% by weight of sodium formate. The pH of the solution was about 6.5. There was also charged to the autoclave 15 grams of a sintered cobalt catalyst containing 20% by weight of cobalt, and then the autoclave pressured to 4000 pounds per square inch with hydrogen and sealed. After being heated for four hours at 225°C the autoclave was opened and the contents analyzed and separated by distillation into a sodium hydroxide stream and a methanol stream. Analysis indicated that about 90% of the sodium formate had been connected to the desired products.

The embodiments of this invention in which an exclusive property or privilege is claimed are defined as follows:

1. A process for hydrogenolysis of an alkali metal or alkaline earth metal salt of formic acid, which process comprises: in a reaction zone contacting a liquid phase solution of said salt of formic acid with hydrogen in contact with a catalyst having a catalytically active surface consisting essentially of metallic cobalt, rhenium, ruthenium, palladium, or platinum or mixtures thereof, said reaction zone being maintained at elevated temperatures and pressures sufficient to cause reaction of said salt of formic acid with said hydrogen to form methanol and a hydroxide of said alkali metal or alkaline earth metal, and withdrawing the reaction products from said reaction zone and separating said hydroxide therefrom.

2. The process of claim 1 wherein said elevated temperatures and pressures are within the temperatures ranges of 100° to 300°C and within the pressure ranges of 75 to 500 atmospheres absolute.

3. The process of claim 2 wherein a catalyst having a catalytically active surface of cobalt is utilized.

4. The process of claim 3 wherein said salt is sodium formate and said solution is an aqueous solution.

5. The process of claim 3 wherein said solution consists essentially of an aqueous solution of sodium formate derived from the production of pentaerythritol by reacting formaldehyde with acetaldehyde in the presence of an alkali or alkaline earth metal hydroxide.

6. The process of claim 1 wherein said salt is a sodium salt.

7. The process of claim 1 wherein a catalyst having a catalytically active surface consisting essentially of metallic cobalt is utilized.

8. The process of claim 1 wherein said solution is an aqueous solution.

9. The process of claim 1 wherein said solution is in a solvent medium selected from the group consisting of water, an alcohol, an ether or mixtures thereof.

10. A process for hydrogenolysis of an alkali metal or alkaline earth metal salt of formic acid, which process comprises: in a reaction zone contacting a liquid phase solution of said salt of formic acid with hydrogen in contact with a catalyst having a catalytically active surface consisting essentially of metallic cobalt, rhenium, ruthenium, palladium, or platinum or mixtures thereof, said reaction zone being maintained at a temperature within the range of 175° to 275°C and a pressure within the range of 125 to 400 atmospheres absolute, said temperatures and pressure being at least that sufficient to cause reaction of said salt with said hydrogen to form methanol and a hydroxide of said alkali metal or alkaline earth metal, and withdrawing the reaction products from said reaction zone and separating said hydroxide therefrom.

11. The process of claim 10 wherein said liquid phase solution is an aqueous solution of sodium formate and wherein a catalyst having a catalytically active surface of cobalt is utilized.

* * * * *